US00PP28327P2

(12) United States Plant Patent
Van Dijk

(10) Patent No.: US PP28,327 P2
(45) Date of Patent: Aug. 22, 2017

(54) *ANTHURIUM* PLANT NAMED 'ANTHERZEK'

(50) Latin Name: ***Anthurium andreanum* L.**
Varietal Denomination: ANTHERZEK

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 14/999,747

(22) Filed: Jun. 22, 2016

(51) Int. Cl.
*A01H 5/02* (2006.01)

(52) U.S. Cl.
USPC ..... Plt./366

(58) Field of Classification Search
USPC ..... Plt./366
See application file for complete search history.

(56) References Cited

PUBLICATIONS

PLUTO Plant Variety Database May 12, 2017. p. 1.*

* cited by examiner

*Primary Examiner* — Annette Para

(74) *Attorney, Agent, or Firm* — Jondle & Associates, P.C.

(57) ABSTRACT

A new compact *Anthurium* plant named 'ANTHERZEK' particularly distinguished by having shiny, white, cordate and very durable spathes that retain the original color for a very long period of time, dark green and long elliptical cordate, durable leaves, white spadix with yellow tip, early and rich flowering continuously throughout the year and a plant height of 33.0 cm to 37.0 cm, is disclosed.

3 Drawing Sheets

Genus and species: *Anthurium andreanum* L.
Variety denomination: 'ANTHERZEK'.

BACKGROUND OF THE NEW PLANT

The present invention comprises a new and distinct variety of *Anthurium*, botanically known as *Anthurium andreanum* L., and hereinafter referred to by the variety name 'ANTHERZEK'. The new *Anthurium* plant is a product of a planned breeding program conducted by the inventor in Bleiswijk, the Netherlands. The objective of this breeding program was to create a new 33.0 cm to 37.0 cm height plant with white, shiny, cordate and very durable spathes that are flowering continuously throughout the year.

The new variety originated from a cross-pollination made in May 2008 in Bleiswijk, The Netherlands. The female parent was a white *Anthurium* pot plant designated '8214-03' (unpatented), and the male parent was a white *Anthurium* pot plant designated '12206-01' (unpatented).

A single plant was selected from the progeny of the stated cross in March 2010 and has been asexually reproduced repeatedly by tissue culture in Bleiswijk, The Netherlands over a 6-year period. The present invention has been found to retain its distinctive characteristics through successive asexual propagations.

Plant Breeder's Rights for this variety have been applied for in the European Union on Nov. 6, 2014. 'ANTHERZEK' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, white, cordate spathe;
2) White spadix with yellow tip;
3) Green elliptical cordate leaves; and
4) Older spathes that become greenish with time.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 34-week old plant grown in a greenhouse in Bleiswijk, The Netherlands in March 2016. Colors in the photographs may differ from the color values cited in the detailed botanical description, which accurately describe the actual colors of the new variety.

DESCRIPTION OF THE NEW VARIETY

Figure 1:
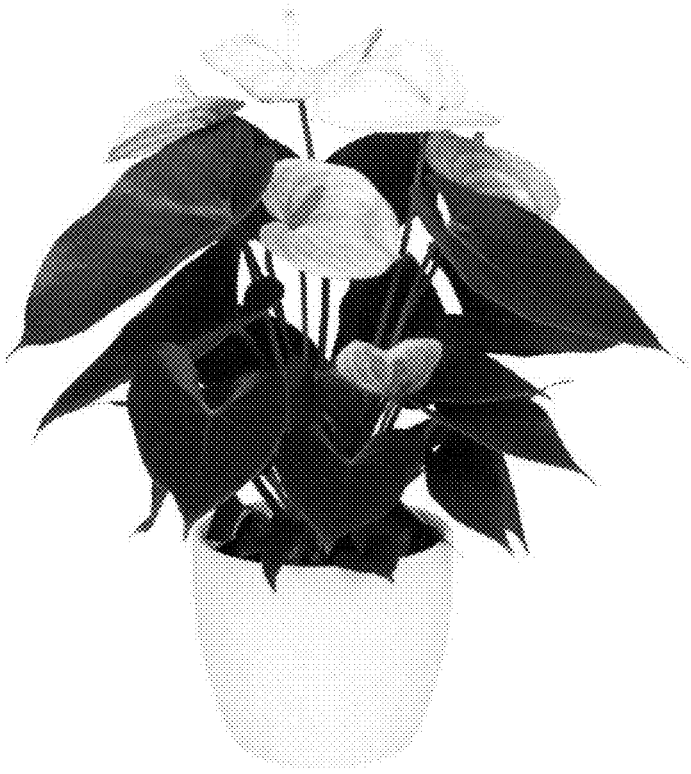
FIG. 1 shows the overall plant habit, including blooms and foliage.
Figure 2:
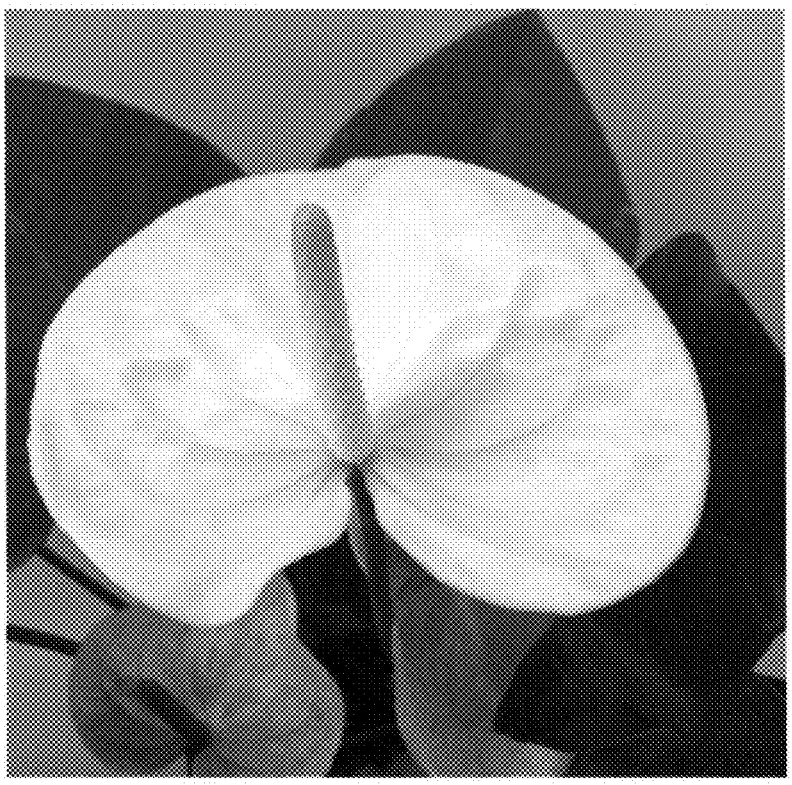
FIG. 2 shows a close-up of the mature spathe.
Figure 3:
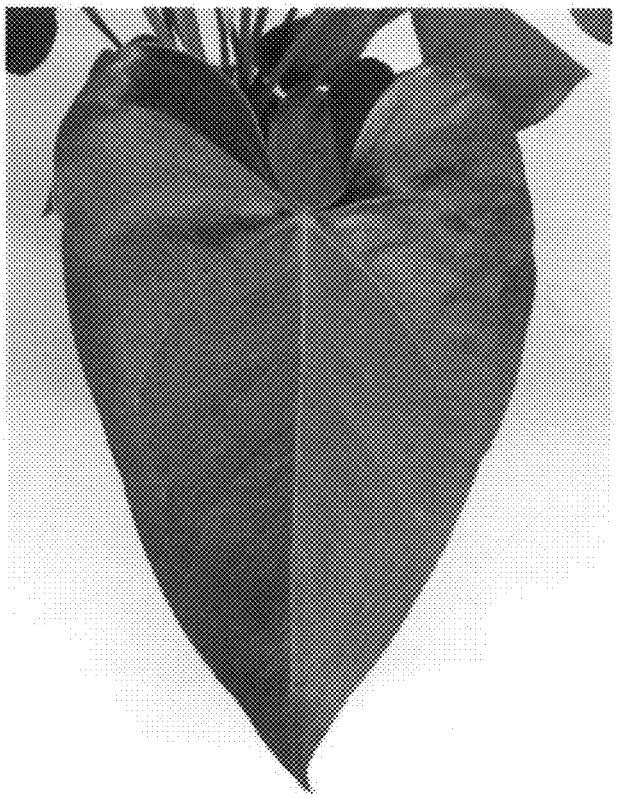
FIG. 3 shows a close-up of the upper leaf blade surface.

The following detailed description sets forth the distinctive characteristics of 'ANTHERZEK'. The data which define these characteristics were collected from asexual reproductions carried out in Bleiswijk, The Netherlands. The plant history was taken on 34-week old plants which were planted from tissue culture in 12-centimeter (diameter) pots and grown in a glass greenhouse between 19° C. and 24° C. Observations were made in March 2016. Color readings were taken under 5000 lux natural light in the greenhouse.

Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andreanum* L.

*Common name*.—*Anthurium*.

*Denomination*.—'ANTHERZEK'.

Parentage:

*Female parent*.—*Anthurium* plant '8214-03' (unpatented).

*Male parent*.—*Anthurium* plant '12206-01' (unpatented).

Plant:

*Propagation*.—Tissue culture.

*Root description*.—Fleshy-creamy colored roots with small hairy lateral roots having yellow-colored root tips.

*Time to produce a finished flowering plant*.—30 to 34 weeks after planting in a 12 cm (diameter) pot.

*Growth habit*.—Herbaceous perennial.

*Height* (*measured from soil, including inflorescence*).—33.0 cm to 37.0 cm.

*Width* (*measured from leaf tips*).—39.0 cm to 43.0 cm.

Leaves:

*Immature leaves*.—Length: 14.0 cm to 16.0 cm. Width: 7.0 cm to 9.0 cm. Color: Upper surface: RHS 146A. Lower surface: RHS 146B. Texture (both upper and lower surfaces): Shiny.

*Mature leaves*.—Length (fully expanded): 18.0 cm to 20.0 cm. Width: 11.0 cm to 13.0 cm. Shape: Elliptical cordate. Apex: Acuminate. Base: Cordate. Leaf blade angle with the petiole: Between 110 degrees and 125 degrees. Leaf margin: Entire. Color: Upper surface: RHS 147A. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Arrangement: Leaf blade has two lobes extending past the petiole. The lobes are non-touching. Length of lobes of mature leaf blades: 3.5 cm to 4.5 cm. Width of lobes of mature leaf blades: 5.0 cm to 6.0 cm. Distance for petiole/leaf junction to highest point on lobes of mature leaf blades: 4.5 cm to 5.5 cm.

*Petiole*.—Cross-section: Round. Diameter: 0.4 cm to 0.45 cm. Length: 18.0 cm to 21.0 cm for a mature leaf size. Color: Mature leaf: RHS 144A. Immature leaf: RHS 144B. Cataphyll color surrounding the petiole: Outside: RHS 144B. Inside: RHS 144C to 144D.

*Geniculum*.—Length: 1.2 cm to 1.7 cm. Width: 0.4 cm to 0.45 cm. Color: RHS 144A.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 85 degrees and 90 degrees; the spathe stands on a wiry peduncle about 1.0 cm to 6.0 cm above the foliage.

*Shape*.—Cordate.

*Apex*.—Cordate.

*Base*.—Acute.

*Texture*.—Shiny and blistered.

*Margin*.—Entire.

*Size*.—Length: 11.5 cm to 12.5 cm. Width: 10.5 to 11.5 cm.

*Lobes*.—Arrangement: The spathe has two lobes extending past the peduncle. The lobes are non-touching. Length: 2.5 cm to 3.5 cm. Width: 5.0 cm to 6.0 cm.

*Color*.—Just fully open: Upper surface: RHS NN155B. Lower surface: RHS NN155C. This white color remains for a very long period, at least more than 20 weeks after opening. After some weeks, the base of the spathe turns greenish.

Peduncle:

*Shape*.—Erect.

*Cross-section*.—Round.

*Length*.—24.0 cm to 27.0 cm.

*Diameter*.—0.37 cm to 0.42 cm.

*Color*.—RHS N144A.

Flowering time:

*General*.—One small rooted untreated tissue culture plant of 8.0 cm tall will flower, depending on season, after 28 to 32 weeks and 4 to 6 blossoms will appear. More blossoms appear after some additional weeks so that a full flowering and commercial plant will have 5 to 7 white spathes. Smaller blossoms may occur on less mature plants.

Spadix:

*Size*.—Length: 3.7 cm to 4.0 cm. Width (at apex): 0.5 cm to 0.6 cm. Width (at base): 0.6 cm to 0.7 cm.

*Shape*.—Columnar.

*Angle from spadix tip to peduncle*.—165 degrees to 180 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 13A and 151D. Mature: RHS 155B. Ages to: RHS 144A.

Flowers:

*Quantity per spadix*.—150 to 200.

*Spadix flower arrangement*.—Bisexual, rounded in cross-section.

*Shape*.—Rounded.

*Size*.—Length: 0.05 cm to 0.10 cm. Diameter (maximum): 0.10 cm. Color: RHS 156D.

Reproductive organs:

*Stamens*.—Not visible.

*Pollen amount*.—Absent.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed.

COMPARISON WITH PARENTAL AND COMMERCIAL VARIETIES

The female parent of 'ANTHERZEK', cultivar '8214-03' (unpatented), is no longer in existence, so a meaningful comparison cannot be made.

'ANTHERZEK' differs from the male parent plant '12206-01' (unpatented) in that 'ANTHERZEK' has elliptical cordate shaped leaves, and weak blistering of the leaf blade upper surface, whereas '12206-01' has ovate cordate shaped leaves and medium blistering of the leaf blade upper surface. Additionally, 'ANTHERZEK' has darker green leaf venation than that of '12206-01'.

'ANTHERZEK' differs from commercial variety 'ANTHCAPBUK' (unpatented) in that 'ANTHERZEK' has cordate shaped spathes with an acute shaped apex, whereas 'ANTHCAPBUK' has orbicular cordate shaped spathes with a mucronate shaped apex. Additionally, 'ANTHERZEK' has longer spathes and spathe lobes than those of 'ANTHCAPBUK'.

'ANTHERZEK' differs from commercial variety 'ANTHDUPAI' (unpatented) in that 'ANTHERZEK' has cordate shaped spathes with an acute shaped apex, whereas 'ANTHDUPAI' has orbicular cordate shaped spathes with a mucronate shaped apex. Additionally, 'ANTHERZEK' has longer spathes and spathe lobes than those of 'ANTHDUPAI'.

I claim:

1. A new and distinct variety of *Anthurium* plant named 'ANTHERZEK', substantially as illustrated and described herein.

* * * * *